US009889084B2

(12) United States Patent
Bleyer et al.

(10) Patent No.: US 9,889,084 B2
(45) Date of Patent: Feb. 13, 2018

(54) COMPOSITIONS OF COSMETIC, PERSONAL CARE AND SKIN CARE PRODUCTS DERIVED FROM LIPID FEEDSTOCKS AND METHODS TO PRODUCE THE SAME

(71) Applicants: James Robert Bleyer, Maumee, OH (US); Jennifer L. Aurandt, Brighton, MI (US); Raymond Paul Roach, Midland, MI (US)

(72) Inventors: James Robert Bleyer, Maumee, OH (US); Jennifer L. Aurandt, Brighton, MI (US); Raymond Paul Roach, Midland, MI (US)

(73) Assignee: Valicor, Inc., Dexter, MI (US)

( * ) Notice: Subject to any disclaimer, the term of this patent is extended or adjusted under 35 U.S.C. 154(b) by 0 days.

(21) Appl. No.: 14/594,572

(22) Filed: Jan. 12, 2015

(65) Prior Publication Data
US 2015/0196482 A1 Jul. 16, 2015

Related U.S. Application Data

(60) Provisional application No. 61/925,934, filed on Jan. 10, 2014, provisional application No. 62/062,286, filed on Oct. 10, 2014.

(51) Int. Cl.
| | |
|---|---|
| A61K 8/02 | (2006.01) |
| A61K 8/92 | (2006.01) |
| A61K 31/047 | (2006.01) |
| A61K 8/34 | (2006.01) |
| A61K 31/355 | (2006.01) |
| A61K 8/67 | (2006.01) |
| A61Q 19/00 | (2006.01) |
| C10L 1/02 | (2006.01) |
| C10M 101/04 | (2006.01) |
| C07C 67/03 | (2006.01) |
| A23D 9/007 | (2006.01) |
| C11B 3/00 | (2006.01) |
| C11B 3/10 | (2006.01) |
| C11B 3/14 | (2006.01) |
| C11B 7/00 | (2006.01) |
| C11C 3/00 | (2006.01) |
| A61K 8/36 | (2006.01) |
| A61K 8/37 | (2006.01) |
| A23K 10/38 | (2016.01) |
| A23K 20/179 | (2016.01) |
| A23K 20/111 | (2016.01) |
| A23K 20/158 | (2016.01) |
| A23K 50/10 | (2016.01) |
| A23K 50/75 | (2016.01) |
| A23K 50/30 | (2016.01) |
| A61Q 3/02 | (2006.01) |
| A61Q 5/02 | (2006.01) |

(Continued)

(52) U.S. Cl.
CPC .............. *A61K 8/922* (2013.01); *A23D 9/007* (2013.01); *A23K 10/38* (2016.05); *A23K 20/111* (2016.05); *A23K 20/158* (2016.05); *A23K 20/179* (2016.05); *A23K 50/10* (2016.05); *A23K 50/30* (2016.05); *A23K 50/75* (2016.05); *A61K 8/342* (2013.01); *A61K 8/345* (2013.01); *A61K 8/361* (2013.01); *A61K 8/375* (2013.01); *A61K 8/678* (2013.01); *A61K 8/925* (2013.01); *A61K 31/047* (2013.01); *A61K 31/355* (2013.01); *A61Q 19/00* (2013.01); *C07C 67/03* (2013.01); *C10L 1/02* (2013.01); *C10L 1/026* (2013.01); *C10M 101/04* (2013.01); *C11B 3/001* (2013.01); *C11B 3/006* (2013.01); *C11B 3/10* (2013.01); *C11B 3/14* (2013.01); *C11B 7/0075* (2013.01); *C11C 3/003* (2013.01); *A61K 2800/10* (2013.01); *A61Q 3/02* (2013.01); *A61Q 5/02* (2013.01); *A61Q 5/12* (2013.01); *A61Q 17/04* (2013.01); *Y02E 50/13* (2013.01); *Y02P 60/873* (2015.11)

(58) Field of Classification Search
CPC ...................................................... A61K 8/922
USPC ........................................................ 424/401
See application file for complete search history.

(56) References Cited

U.S. PATENT DOCUMENTS

| | | | | |
|---|---|---|---|---|
| 6,136,301 | A * | 10/2000 | Pelle .................. | A61K 8/37 424/401 |
| 2011/0280918 | A1* | 11/2011 | Shinitzky ................. | A23L 1/30 424/401 |
| 2013/0142881 | A1* | 6/2013 | Odom .................. | A61K 35/644 424/537 |

OTHER PUBLICATIONS

Palombo (Skin Pharmacol Physiol 2007;20:199-210).*
Majoni (J Am Oil Chem Soc (2010) 87:205-213).*

* cited by examiner

*Primary Examiner* — Devang K Thakor
(74) *Attorney, Agent, or Firm* — Kohn & Associates, PLLC

(57) ABSTRACT

Lipid compositions and lipid compositions included in cosmetic products, personal care products, skin care products, nutraceuticals, bio fuels, bio-lubricants, oleo chemicals, nutritional products, other bio-products, and animal feed compositions. Concentrations of lipid components. A method of removing and recovering a lipid composition by mixing a lipid feedstock with a solvent, separating the mixture into a raffinate phase and an extract phase containing beneficial non-glyceride compounds, removing solvent from the extract phase and obtaining a concentrate phase, and recovering a lipid composition from the concentrate phase. A method of producing a fatty acid alkyl ester. A method of producing a distiller's product. A method of performing secondary extractions and recovering a lipid composition by performing a first extraction on a lipid feedstock, performing a second extraction on a lipid feed- (Continued)

stock, and exploiting differences in solubility limits to create unique product fractions derived from naturally occurring lipids.

6 Claims, 6 Drawing Sheets

(51) Int. Cl.
*A61Q 5/12* (2006.01)
*A61Q 17/04* (2006.01)

COMPOSITIONS OF COSMETIC, PERSONAL CARE AND SKIN CARE PRODUCTS DERIVED FROM LIPID FEEDSTOCKS AND METHODS TO PRODUCE THE SAME

BACKGROUND OF THE INVENTION

1. Technical Field

The present invention relates to compositions comprising lipids and beneficial lipid soluble non-glyceride compounds and methods to produce such compositions. More specifically, the present invention relates to compositions for use in cosmetic, personal care and skin care applications and methods to produce such compositions.

2. Background Art

The cosmetic, personal care, and skin care industry uses a myriad of plant, vegetable, fruit, and seed oils in formulations such as treatment creams, massage and bath products, skin cleansing, and hair conditioning products.

These oils contain lipids; such as waxes, fatty acids, sterols and lipid soluble components; such as tocopherols and carotenoids, and have a variety of properties and functionalities.

Coverage of the upper layer of the skin with natural oils reduces trans-epidermal water loss (TEWL) and maintains water in the upper layer of the skin contributing to enhanced hydration. TEWL is a measure of barrier integrity and is defined as the quantification of water that passes from inside the body through the skin to the surrounding atmosphere via diffusion and evaporation. The stronger the barrier, the lower the TEWL.

The fatty acids can be non-essential fatty acids; such as oleic, palmitic, palmitoleic, lauric, and stearic acids or essential fatty acids; such as linoleic and linolenic. Fatty acids can be saturated (stearic, caprilic, palmitic) or unsaturated (oleic, linoleic) and can exist in their free form or as glycerol esters. They can be used in their anhydrous state or as an oil/water emulsion. Fatty acids are used primarily as a skin conditioner and as a carrier for other components.

Fatty acids are an important component of the skin's intracellular lipid lamellae matrix and human sebum. Human sebum includes more than 40% fatty acids; therefore, selected acids, when applied, can partition into the sebum and the follicular opening. Fatty acids are also part of the outer layer of the skin, the stratum corneum. The skin's barrier properties are partially dependent upon the unique organization of ceramides, sterols (mostly cholesterol), and free fatty acids arranged as extra-cellular lamellar bilayers between corneocytes.

Individual fatty acids have particular functionality with respect to cosmetic and skin care applications. For example, oleic acid has been shown to enhance skin permeation of various active compounds. It is theorized that the mechanism of action attributed for permeation enhancement is fluidization of the organized lamellar organization in the stratum corneum. Linoleic acid is known to play a role in maintaining an intact stratum corneum layer and to elevate the rate of epidermal cell proliferation and therefore skin renewal. Skin disorders such as eczema, psoriasis and dermatitis have been related to deficiencies in linoleic acid. Palmitoleic acid was found to exhibit anti-microbial activity effective against gram positive bacteria, suggesting usefulness in topical formulations for treatment of secondary gram positive bacterial infections.

Fatty acids are also used as a carrier for other lipids and lipid soluble compounds such as phytosterols, tocopherols, tocotrienes, and carotenoids. These compounds absorb more efficiently when combined with specific fatty acids. However, topically applied esterified fatty acids such as triacylglycerols must first be cleaved to their free acid form by lipase enzymes present in eccrine/sebaceous secretions. Topically applied free fatty acids can be absorbed directly. The kinetics of absorption of topically applied lipids and lipid soluble compounds increase with increasing ratios of free fatty acids to acyl glycerides.

Phytosterols are a naturally occurring plant sterol. It is well known that phytosterols have anti-inflammatory properties and are used in personal care products including anti-aging products. The breakdown and loss of collagen is a contributing factor to the aging of skin. Unprotected exposure to the sun accelerates this aging phenomenon. According to a study by Germany's National Institute of Health, topical treatments containing phytosterols are effective in blocking the reduced collagen synthesis after UV irradiation and have stimulatory effects. The study concluded phytosterols "may be useful additions to anti-aging products".

Tocopherols and tocotrienes are valuable in skin care applications for their anti-oxidant properties that protect against DNA damage caused by environmental free radicals that promote premature aging. α-Tocopherol is an antioxidant responsible for quenching lipid peroxyl free radicals thereby protecting against acute and chronic UV-induced damage. Collagen synthesis and inhibition of collagen degradation was enhanced with tocopherol application thereby preventing wrinkle formation and preserving skin elasticity. In addition, tocopherols exhibit anti-inflammatory activity by decreasing prostaglandin signaling.

Carotenoids are also incorporated into skin care products to counteract premature aging caused by free radicals. Carotenoids are naturally occurring plant pigments that protect plants against excessive exposure to UV radiation and have been shown to provide photoprotection to light exposed human tissue. The human skin, as the boundary organ between the human body and the environment, is under the constant influence of free radicals (FR), both from the outside in and from the inside out. Carotenoids are known to be powerful antioxidant substances playing an essential role in the reactions of neutralization of FR (mainly reactive oxygen species ROS). Carotenoid molecules present in the tissue are capable of neutralizing FR, especially ROS, and are then destroyed. In a study published in Skin Pharmacol Physiol, it was shown that this UV protection is imparted with either oral ingestion or topical application and an accretive effect was demonstrated with combined oral ingestion and topical application.

In addition to their role in promoting skin health, carotenoids also have applications in beauty products. These plant pigments accumulate in the stratum corneum causing a yellow/red coloring of the skin, giving a healthier and more attractive appearance. As with the use of carotenoids for UV protection, the benefit of using carotenoids for skin coloration occurs whether the carotenoids are administered through oral ingestion or topical application.

The cosmetic, personal care and skin care industry desires natural and naturally derived products. Therefore there is a need for a composition derived from a naturally occurring lipid containing concentrations of compounds with desirable functionalities and a method to produce such compositions.

The cosmetic industry places a high value on these compositions. However, by-products and co-products are also created and uses for these products must also be found to contribute to the economic feasibility of the processes described herein. The expanded use of the products of the present invention add to the process economy of scale.

Rudolph Diesel developed the diesel engine in the 1890's. Because of its high power, efficiency and reliability, the diesel engine became the engine of choice for demanding applications. Rudolph Diesel envisioned the use of lipids as the fuel for this engine. However, the widespread discovery of petroleum oil made petroleum based diesel fuel cheap and abundant and it quickly became the fuel of choice for diesel engines.

Recent concern over the diminution of petroleum reserves and the environmental effects of diesel fuel has led to the search for alternative fuels for diesel engines. The products of the present invention are highly desirable as alternative energy feedstocks.

Environmental concerns are also driving the search for alternatives for other oleo chemical products, such as bio lubricants, foams, plastics, dielectric fluids, solvents, paints and coatings.

There is also a desire to produce animal feed products. Laying hens are fed lutein to give egg yolks a more desirable color. Isolated palmitic acid added to the finishing diet of beef cattle is known to improve marbling. The hog industry desires specific saturated/unsaturated fats ratios to promote leaner pork products.

Isolation and recovery of beneficial lipid-soluble non-glyceride compounds from various bio-based feedstocks has been practiced for many years. Fernandes and Cabral [Bioresource Technology 98 (2007) 2335-2350] reviewed recovery methods for phytosterols, with the most common methods involving recovery from distillates obtained during the deodorization of crude vegetable oils. Deodorizer distillates, especially of soy, corn, wheat germ and tall oil are enriched in phytosterols and hence are preferred feedstocks for recovering purified concentrates of these beneficial compounds. The methods addressed by Fernandes and Cabral are focused on obtaining phytosterol concentrates in excess of 50 wt % and more typically greater than 80 wt %. Many of the common recovery methods involve hydrolysis and saponification of esters followed by distillation of the unsaponifiable compounds, including phytosterols.

Rodrigues, et al. [Recent Patents on Engineering 1 (2007) 95-102] reviewed published methods for deacidification of vegetable oils, i.e. removal of free fatty acids (FFAs). Traditional deacidification approaches include chemical, physical and solvent extraction methods. Newer approaches include biological removal of FFAs by microorganisms and enzymatic esterification, supercritical fluid extraction and membrane processing. Rodrigues, et al. highlighted solvent extraction with short chain alcohols, alcohol/water mixtures and other polar solvents as particularly useful for deacidification of crude vegetable based oils; however, the focus is on removal of FFAs with retention of tocopherols and tocotrienols in the raffinate oil rather than isolation and recovery of these beneficial non-glyceride compounds in the solvent extract. In several cited examples, Rodrigues et al. show that addition of water (up to 20% w/w) to an alcohol helps to reduce the amount of neutral oil (triglycerides) lost to the solvent, yet the solvent retains FFA removal power. A further consequence of increasing water concentration in an alcohol/water solvent mixture is that beneficial non-glyceride compounds such as tocopherols, sterol ester and carotenoids partition to the raffinate phase. Thus water concentration in an alcohol solvent can be used to tailor the partitioning of glycerides and non-glycerides in the extract and raffinate phases. Solvent extraction has been applied to many plant based oils including canola, coconut, corn, cottonseed, olive, palm, rape, rice bran, sesame seed and various nut oils.

The tremendous growth of the United States ethanol industry over the past ten years has also resulted in the growth of ethanol byproducts including distillers dry grain with solubles (DDGS) and distillers oil (DO). Ethanol, DDGS and DO yields are currently about 21, 17.7, and 0.5 pounds per bushel of corn respectively (1 bushel=56 pounds shelled corn at 15.5 wt % moisture). Technology improvements are expected to increase DO yields to over 1 pound per bushel. Most US dry grind ethanol plants have installed DO recovery systems and hence a supply of almost 4 billion pounds of DO is theoretically available in the nearly 13.3 billion gallon US ethanol market.

Although corn is the predominant grain used for producing ethanol in the United States, milo, barley, wheat and other grains are also used. In the case of these other feedstocks, analogous distillers oil can also be recovered. Distillers oil produced primarily from corn fermentation is known as distillers corn oil (DCO) but can contain oils of other grains if fermented in the same facility. The term DO as applied herein refers generically to any oil recovered from a grain fermentation process, including corn.

In the conventional dry grind ethanol process, grain is ground, slurried in water, cooked and treated with enzymes to convert starch to sugars. Yeast then convert the sugars to ethanol and carbon dioxide during fermentation resulting in an ethanol rich "beer". Ethanol is removed from the beer by distillation resulting in "whole stillage," an aqueous slurry of unfermented dissolved and suspended corn solids. Whole stillage is separated with a decanting centrifuge into distillers wet grains containing the bulk of the suspended solids of whole stillage and thin stillage containing dissolved solids, fine suspended solids, protein and oil. Up to one half of the thin stillage is recycled to the cook step and the balance is concentrated to "syrup" in multi-effect evaporators. Distillers oil is typically obtained by centrifugation of partially concentrated thin stillage but can be recovered at various parts of the process. Syrup may be sold as is or mixed with distillers wet grains and dried to produce DDGS.

Investigators have shown that DCO has a composition distinctly different from crude germ oil or refined germ oil, i.e. edible corn oil for human consumption (Moreau et al., J. Am. Oil Chem. Soc. 2010, 87, 895-902; Winkler-Moser, Industrial Crops and Products 2011, 33, 572-578). Moreau et al. showed that free fatty acids in post fermentation corn oil (DCO) are 11-16% w/w, much higher than crude ethanol extracted whole kernel oil having about 1% w/w FFA or commercial edible oil (corn germ oil, refined, bleached and deodorized) having no measurable FFA. With respect to beneficial non-glyceride compounds, the levels of free phytosterols and hydroxycinnamate sterylesters in DCO were higher than those of corn germ oil and were comparable to those of ethanol-extracted corn kernel oil. The levels of tocopherols were lower in DCO than in either corn germ oil or ethanol extracted corn kernel oil. The levels of lutein and zeaxanthin in DCO were much higher than those in corn germ oil and were comparable to those in ethanol-extracted corn kernel oil. Thus DCO and other distillers oils offer valuable depots of FFAs and beneficial non-glyceride compounds if a cost-effective recovery process can be developed. The present invention provides for compositions and cost effective methods of obtaining valuable lipid compositions from distillers oil and other natural lipid sources.

Distillers oil is primarily sold as an animal feed component or as a feedstock for the production of fatty acid methyl esters (biodiesel). As a biodiesel feedstock, distillers oil commands a lower price than soybean oil due to distillers oil's relatively high free fatty acid content (>10 wt %). Modern ethanol plants continually strive to maximize the financial return on each bushel of purchased grain. A high value oil composition produced from distillers oil and enriched in beneficial lipid soluble non-glyceride compounds offers the ethanol producer a further opportunity to improve their financial return on grain.

U.S. Pat. No. 8,702,819 assigned to Poet Research Inc. discloses a corn oil composition containing less than 5 wt % free fatty acids and greater than threshold levels of specific carotenoids, e.g. greater than 50 micrograms/g lutein. Poet further discloses a method of obtaining the low FFA oil composition by treating DCO with alkali. Alkali neutralizes (saponifies) the free fatty acids making them much less oil soluble and de-emulsifies the oil for improved oil/water phase separation. The Poet patent emphasizes production of low FFA oil; however, the recovery of an oil composition enriched in beneficial lipid soluble non-glyceride compounds is not disclosed.

Therefore there is a need for efficient methods to produce compositions derived from low cost naturally occurring lipids containing concentrations of compounds with desirable functionalities.

SUMMARY OF THE INVENTION

The present invention provides for a lipid composition including free fatty acids of about 15% w/w or greater, triglycerides of about 75% w/w or less, and at least one beneficial non-glyceride compound chosen from the group of $\alpha$-tocopherol, of about 50 ppm w/w or greater, total tocopherols of about 2000 ppm w/w or greater, total carotenoids of about 300 ppm w/w or greater, lutein of about 150 ppm w/w or greater, zeaxanthin of about 100 ppm w/w or greater, and total sterols of about 2000 ppm w/w or greater.

The present invention provides for a lipid composition including triglycerides content not less than 96% w/w, free fatty acids content not greater than 4% w/w, total moisture and insolubles content not greater than 1.5% w/w, total carotenoid content not greater than 50 ppm w/w, and at least one component selected from the group consisting of total lutein content not greater than 50 ppm w/w, cis-lutein/zeaxanthin content not greater than 10 ppm w/w, $\alpha$-cryptoxanthin content not greater than 5 ppm w/w, $\beta$-cryptoxanthin content not greater than 5 ppm w/w, $\alpha$-carotene content not greater than 0.5 ppm w/w, and cis-$\beta$-carotene not greater than 0.1 ppm w/w.

The present invention provides for a lipid composition including: free fatty acids of about 5% w/w or less and total carotenoids of about 500 ppm w/w or greater.

The present invention provides for a composition including a concentration of a lipid component wherein the concentration w/w of the lipid component is at least twice a concentration of the lipid component in a lipid feedstock, selected from the group of free fatty acids, $\alpha$-tocopherol, total tocopherols, total carotenoids, lutein, zeaxanthin, and total sterols.

The present invention provides for a composition including a concentration of a lipid component wherein the concentration w/w of the lipid component is one half or less of a concentration of the lipid component in a lipid feedstock, selected from the group of free fatty acids, $\alpha$-tocopherol, total tocopherols, total carotenoids, lutein, zeaxanthin, and total sterols.

The present invention further provides for a method of removing and recovering a lipid composition including the steps of mixing a lipid feedstock with a solvent, separating the mixture into a raffinate phase and an extract phase containing beneficial non-glyceride compounds, removing solvent from the extract phase and obtaining a concentrate phase, and recovering a lipid composition from the concentrate phase.

The present invention provides for a lipid composition produced by the above method.

The present invention provides for a lipid composition including a phospholipid content greater than that of a feedstock.

The present invention also provides for a method of producing a fatty acid alkyl ester, including the steps of, extracting a lipid feedstock with an alcohol to produce an extract phase and a low free fatty acid (FFA) raffinate phase, reacting the low FFA raffinate with alcohol to produce a fatty acid alkyl ester, recovering excess alcohol from said reacting step, and recycling recovered alcohol to said extraction step.

The present invention also provides for a method of producing a distiller's product, including the steps of separating a lipid from a fermentation process, mixing the lipid with a solvent and obtaining a lipid/solvent mixture, separating the lipid/solvent mixture into two or more fractions, and adding at least some of the one or more fractions to at least a portion of fermentation stillage.

The present invention further provides for a method of removing and recovering a lipid composition, including the steps of mixing a lipid feedstock with a solvent, separating the mixture into a raffinate phase and an extract phase, removing solvent from the extract phase and obtaining a first concentrate phase, mixing the raffinate phase with a second solvent, separating the mixture into a second raffinate phase and a second extract phase, removing the second solvent from the second extract phase and obtaining a second concentrate phase, and recovering a lipid composition from the first and second concentrate phases.

The present invention provides for a method of performing secondary extractions and recovering a lipid composition, including the steps of performing a first extraction on a lipid feedstock, performing a second extraction on a lipid feedstock, and exploiting differences in solubility limits to create unique product fractions derived from naturally occurring lipids.

The present invention also provides for a cosmetic, personal care, or skin care product including the lipid compositions above.

The present invention provides for nutraceuticals, bio fuels, bio-lubricants, oleo chemicals, nutritional products and other bio-products including the lipid compositions above.

The present invention provides for an animal feed composition including the lipid compositions above.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
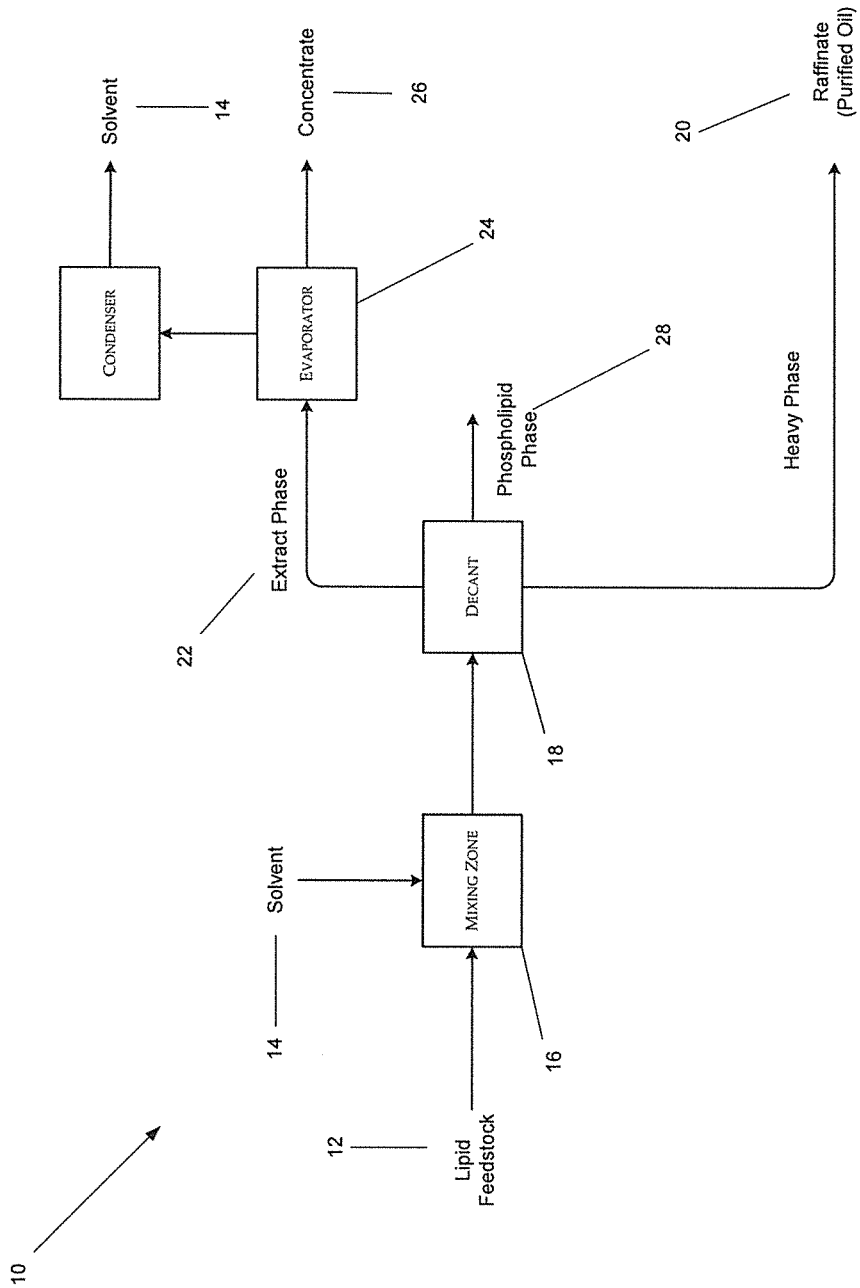
FIG. 1 is a flowchart of a first embodiment of the invention in which a lipid feedstock is mixed with a solvent and allowed to separate to produce a light phase and heavy phase of purified oil and solvent is removed from the light phase to produce a concentrate of beneficial non-glyceride compounds.

The present invention generally provides for compositions recovered from a naturally occurring lipid. The compositions can include lipids, lipid and lipid soluble compounds, and specific combinations of lipids and lipid soluble compounds. The present invention also provides for the use of the compositions in a cosmetic, personal care or skin care product or as an additive to such products. The present invention also provides for the use of the compositions as a feedstock for bio-fuel, bio-chemical, bio-product or oleo chemical processes. The present invention further provides for a composition including one or more of the following: triglycerides, diglycerides, free fatty acids, phospholipids, tocopherols, tocotrienols, carotenoids, and sterols. The present invention further provides for methods to produce various concentrations of lipids, lipid and lipid soluble compounds, and various concentrations of specific combinations of lipids and lipid soluble compounds.

The terms "triglycerides" and "triacylglycerides" are used synonymously herein and refer to lipids having a glycerin backbone esterified to three fatty acid (acyl) side chains.

The term "acyl glyceride" as used herein refers to lipids having a glycerin backbone esterified to either one (monoglyceride), two (diglyceride) or three (triglyceride) fatty acids (acyl) side chains.

For simplicity, free fatty acids, tocopherols, tocotrienols, carotenoids, sterols, and other extracted compounds are herein collectively and individually referred to as "extracted compounds".

"Biofuel" as used herein refers to a fuel derived from living matter, whether animal or plant, and preferably contains lipids. The biofuel can be bioethanol, biodiesel or renewable diesel.

"Bio-lubricant" as used herein refers to a substance derived from organic matter, whether animal or plant, used to reduce friction and wear.

"Bio-products" as used herein refers to a chemical or other manufactured product whose primary feedstock is derived from living matter, whether animal or plant.

"Nutraceuticals" as used herein refers to a compound or group of compounds including biological derived compounds that promotes health, increased metabolic function, or general well being of an organism including human and or animals.

"Nutritional product" as used herein refers to a compound or group of compounds that fulfills specific nutritional requirements of an organism including human and or animals.

"Polar" as used herein refers to a compound that has portions of negative and/or positive charges forming negative and/or positive dipoles. While a polar compound does not carry a net electric charge, the electrons are unequally shared between the nuclei. Water is considered a polar compound in the present invention.

"Extract" or "extract phase" as used herein refers to a mixture containing solvent and all compounds solubilized within the solvent in a liquid-liquid extraction process. The extract phase is enriched in one or more solvent soluble compounds originally present in the lipid feed stream treated in the extraction process.

"Concentrate" as used herein refers to the extract or extract phase following removal of the extraction solvent. The solvent can be a mixture of solvents including water.

"Raffinate" or "raffinate phase" as used herein refers to the solvent lean phase produced in a liquid-liquid extraction process. The raffinate phase is partially depleted in one or more components transferred into the solvent/extract phase.

"Beneficial non-glyceride compounds" (or "BNGs") refers to any of a family of lipid soluble non-glyceride compounds including carotenoids, tocopherols, tocotrienols, phytosterols and phytostanols that are soluble in the glyceride lipid fraction of plant based oils and are widely recognized as beneficial in cosmetic, nutraceutical, animal and human nutrition applications. All compounds belonging to these families are characterized by chemical structures possessing one or more cyclic carbon rings and aliphatic or isoprenoid side chains. BNGs containing hydroxyl groups can be found in free and ester forms.

The naturally occurring lipid, herein referred to as "lipid feedstock" can be any lipid produced by plants or animals including, but not limited to, corn oil, soybean oil, coconut oil, rapeseed oil, canola oil, jajoba oil, shea butter, walnut oil, palm oil, palm kernel oil, mustard seed oil, poppy seed oil, linseed oil, hemp oil, rice oil, avocado oil, wheat oil, milo oil, almond oil, apricot oil, borage oil, castor oil, coffee oil, macadamia nut oil, olive oil, sunflower oil, safflower oil, sesame oil, tomato oil, pumpkin oil, peanut oil, cottonseed oil, fish oil, and krill oil. The naturally occurring lipid can be from algae, fungi, or other microorganisms. Thus, in general, the lipid compositions of the present invention can be derived from a seed, plant, vegetable, or animal-based lipid. The lipid compositions can be derived from a lipid byproduct of a fermentation process, such as an alcohol fermentation process.

Mechanical pressing and extraction with various solvents are used to recover lipids and lipid soluble compounds from oil seeds, plant material, and microorganisms. These primary recovery processes and resulting oil products are well known and are not part of the present invention. However, it has been discovered for the first time that secondary extractions of mechanically pressed or primary extracted naturally occurring lipids can exploit differences in solubility limits to create unique product fractions. These unique product fractions have high functionality and usefulness in cosmetics, personal care and skin care products, such as, but not limited to, shampoos, hair lotions, skin lotions, skin protection products, sunscreen lotion, self tanning products, nail creams, and nail polish. These unique product fractions also have high functionality and usefulness in nutraceuticals, bio fuels, bio-lubricants, oleo chemicals, nutritional products, other bio-products, and animal feed compositions. Any of the lipid compositions described herein can be used in the above described products.

Therefore, the present invention provides for a method of performing secondary extractions and recovering a lipid composition, including the steps of performing a first extraction on a lipid feedstock, performing a second extraction on a lipid feedstock, and exploiting differences in solubility limits to create unique product fractions derived from naturally occurring lipids.

There are various solvents that dissolve glycerides, lipids, and BNG's found in lipid feedstocks. Each of these components has unique solubility profile in the solvent. It has been discovered that by exploiting the different solubility profiles, the extracted compounds can be preferentially removed and recovered and unique products can be produced.

A method of secondary extraction and recovery of lipids and lipid soluble compounds is as follows. It should be understood that description of various process steps in this particular method can apply in the other methods described herein. A lipid feedstock is mixed with a solvent in a ratio sufficient to dissolve the desired extracted compounds. Preferably, the solvent added is a polar solvent, such as, but not limited to, low molecular weight aldehydes, ketones (such as acetone), acetates, esters, furans, alcohols having typically fewer than 6 carbon chains such as methanol, ethanol and propanols, diols, polyols, organic acids such as formic, acetic and propionic acid, water, and combinations of solvents. The solvent can be a mixture of a polar solvent containing up to 25% w/w water. Additionally, polar solvents can include amphipathic solvents. Non-polar solvents can also be used. Hexane can be used and is non-polar. Propane can be used as the solvent. Carbon dioxide and/or or super critical carbon dioxide can be used as a solvent. When the feedstock is mixed with a solvent at a proper ratio, most of the extracted compounds dissolve in the solvent, but only a portion of the glycerides dissolve in the solvent, thereby concentrating the extracted compounds.

The lipid feedstock is mixed with the solvent using one of various methods including, but not limited to agitated tank, cavitation pump, static mixer or other suitable mechanisms.

At least some of the solvent and at least some of the extracted compounds dissolved in the solvent, known as the extract phase, are separated from the feedstock-solvent mixture by one of various methods including, but not limited to, quiescent decantation, centrifugation, or other suitable methods. All of the solvent and all of the dissolved extracted compounds can also be removed from the feedstock-solvent mixture.

The solvent can be removed from the extract phase resulting in a non-glyceride concentrate or concentrate phase containing extracted compounds and glycerides. Various methods known to those skilled in the art can be used to remove the solvent including, but not limited to, evaporation, distillation, pervaporation, inert vapor stripping, anti-solvent extraction/washing, and combinations thereof. In anti-solvent washing, the extract phase is mixed with an antisolvent, for example water, such that the solvent dissolves in the antisolvent. The extracts are removed from the antisolvent mixture by methods including, but not limited to, quiescent decantation or centrifugation. Examples of evaporative methods for solvent removal include but are not limited to single stage and multi-stage fractional distillation, wiped or falling film evaporation, steam stripping, pervaporation, and combinations thereof.

Various process variables, such as choice of solvent, mix time, oil temperature, solvent temperature and solvent/feedstock ratios can be changed to achieve the desired concentration of the extracted compounds in the concentrate phase. Various process steps can be performed in a batch or continuous contacting device, such as the mixing and separating steps. A continuous contacting device can operate counter-currently and contain multiple contacting stages.

The material remaining after removal of the extract phase, known as the heavy phase or raffinate phase, is then collected and can be further processed and/or used for various processes and products such as biofuels and bio-lubricants. The raffinate phase can also be used in cosmetic, personal care and skin care products as is or after further processing. Any residual solvent can be removed from the raffinate phase by various evaporative methods known to those skilled in the art including, but not limited to, evaporation (thin film, falling film and wiped film evaporators), distillation (single and multi-stage fractional distillation), inert vapor stripping (such as steam or hot air), anti-solvent extraction, membrane based pervaporation, and combinations thereof. The evaporated solvent can be condensed and recovered. It should be understood that any of the methods described herein can be performed batch-wise or continuously.

In one embodiment of the invention, shown in FIG. 1, a lipid feedstock (12) is mixed with a solvent (14) by any suitable means (16). The mixture is allowed to quiescent decant (18). The raffinate phase (20) is collected as the heavy phase. The extract phase (22) is collected as the light phase. The solvent (14) is evaporated (24) from the extract phase and then condensed and recovered for reuse. The extracted compounds and a portion of the glycerides are recovered as a non-glyceride concentrate or concentrate (26). The raffinate can be considered to be purified oil, rich in triacylglycerides.

Therefore, the present invention provides for a method of removing and recovering a lipid composition by mixing a lipid feedstock with a solvent, separating the mixture into a raffinate phase and an extract phase containing beneficial non-glyceride compounds, removing solvent from the extract phase and obtaining a concentrate phase, and recovering a lipid composition from the concentrate phase.

The concentrate phase can contain high levels of lutein, zeaxanthin, and other carotenoids, tocopherols, tocotrienes, phytosterols, and other sterols. These beneficial non-glyceride compounds have utility in cosmetic applications. Sterols are used for their anti-inflammatory properties. Tocopherols, tocotrienes, and carotenoids are used as antioxidants. Carotenoids are also used as photoprotectants against UV exposure. High concentrations of these compounds are desirable in cosmetic and personal care products because it lowers the required inclusion rate of the lipid carrier and thereby lessens its dilutive effect. Therefore, in one embodiment, the concentrate phase is used as or added to a cosmetic or personal care product.

In one embodiment, a phase enriched in phospholipids can be recovered as a middle phase or phospholipid phase (28). Phospholipids consist of a diglyceride with a phosphate group covalently bonded to a polar organic molecule such a choline. Phospholipids are amphipathic in nature, as they have a polar phosphate and non-polar acyl moieties. This characteristic causes phospholipids present in distillers oil and other natural oils to partition at the solvent-oil interface during extraction, where the acyl groups noncovalently bond with the non-polar raffinate and phosphate component interacts with the polar solvent. Therefore, the present invention provides for a lipid composition including a phospholipid content greater than that of a feedstock. The present invention also provides for a method of producing this lipid composition by recovering the lipid composition from an interfacial layer of a lipid extraction process.

Phospholipids are a natural emulsifier and are used in cosmetic products to make stable oil-in-water emulsions. Phospholipids also support the barrier function of the skin and enhance bio-absorption of associated compounds making them desirable for use in cosmetic products. Therefore, in one embodiment, the phospholipid-enriched phase is used as or added to a cosmetic or personal care product.

In this embodiment of the present invention, the lipid feedstock contains one or more of the following: free fatty acids, diglycerides, triglycerides, tocopherols, tocotrienols, carotenoids, sterols, and other lipid soluble compounds. After mixing with solvent, some or all of the lipids and lipid soluble compounds are recovered from the lipid feedstock/solvent mixture. The solvent phase is preferentially enriched in free fatty acids, diglycerides, tocopherols, tocotrienols, carotenoids, sterols, and other lipid soluble compounds. Beneficial non-glyceride compounds (tocopherols, tocotrienols, sterols, fatty acids, carotenoids free fatty acids, $\alpha$-tocopherol, total tocopherols, total carotenoids, lutein, zeaxanthin, and total sterols) can be concentrated from the lipid composition. This concentrating can be achieved by removing FFAs or glycerides by a method such as shortpath or molecular distillation, saponification and phase separation, chemical or enzymatic hydrolysis of glycerides, liquid-liquid extraction, winterization, esterification, trans-esterification, membranes, chromatography, and combinations thereof. The present invention provides for a lipid composition produced by this method.

The concentration of triglycerides is enriched in the raffinate phase with a concomitant reduction of free fatty acids, diglycerides, tocopherols, tocotrienols, carotenoids, sterols, and other lipid soluble compounds. Solvent is removed from one or more of the recovered phases including the raffinate phase and the extract phase.

Triglycerides are often used as a carrier for lipid soluble components in cosmetic and personal care products. High purity triglycerides are desirable for such applications. Therefore, in one embodiment, the raffinate phase is used as or an additive to a cosmetic or personal care product.

Figure 2:
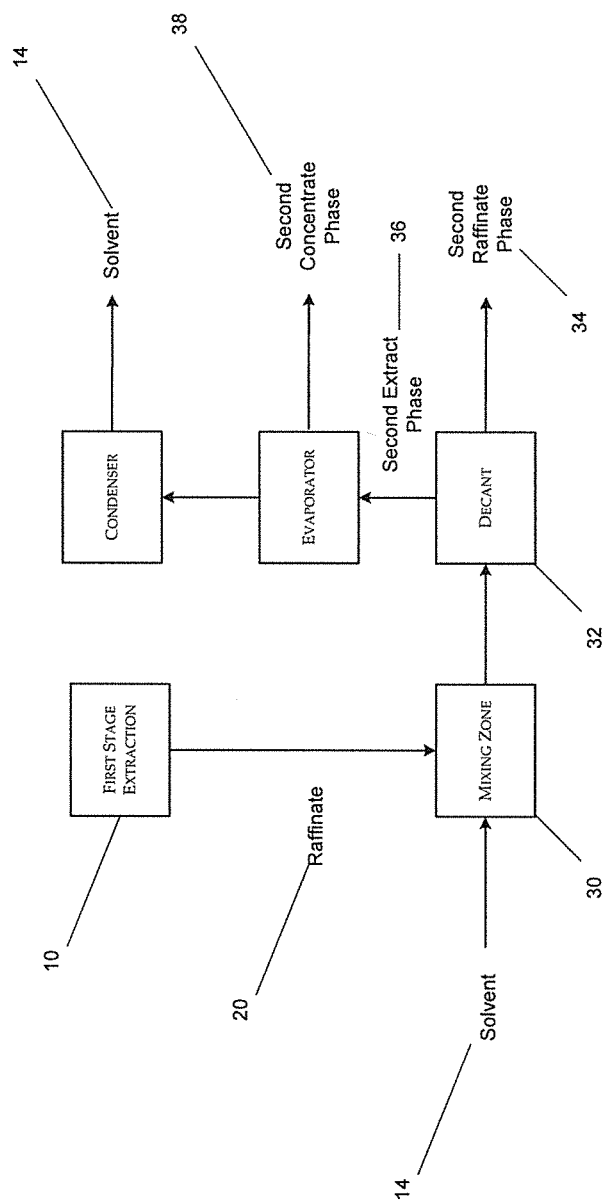
FIG. 2 is a flowchart of a second embodiment of the invention in which the raffinate of FIG. 1 is extracted a second time to improve extraction efficiency.

In another embodiment of the invention, shown in FIG. 2, a lipid feedstock is processed as in FIG. 1 (10) to produce a raffinate (20). The raffinate phase is mixed (30) with a second charge of solvent (14). The second solvent can be the same as the first solvent or a different solvent. The mixture is allowed to quiescent decant (32) into a second raffinate phase (34) and second extract phase (36). The second extract phase is collected as the light phase. The solvent (14) is evaporated from the second extract phase and recovered for reuse and a second concentrate phase (38) is recovered. The second concentrate phase can be optionally combined with the first concentrate.

Therefore, the present invention provides for a method of removing and recovering a lipid composition by mixing a lipid feedstock with a solvent, separating the mixture into a raffinate phase and an extract phase, removing solvent from the extract phase and obtaining a first concentrate phase, mixing the raffinate phase with a second solvent, separating the mixture into a second raffinate phase and a second extract phase, removing the second solvent from the second extract phase and obtaining a second concentrate phase, and recovering a lipid composition from the first and second concentrate phases. The present invention also provides for a lipid composition recovered by this method.

Those skilled in the art will appreciate that the amount of solvent required for the extraction process can be lessened by the use of countercurrent wash steps. In a stage of the countercurrent wash system, lipids are mixed with solvent then allowed to quiescent decant. The light phase which contains the extract phase is moved to the stage upstream. The heavy phase which contains the raffinate phase is moved to the stage downstream.

Figure 3:
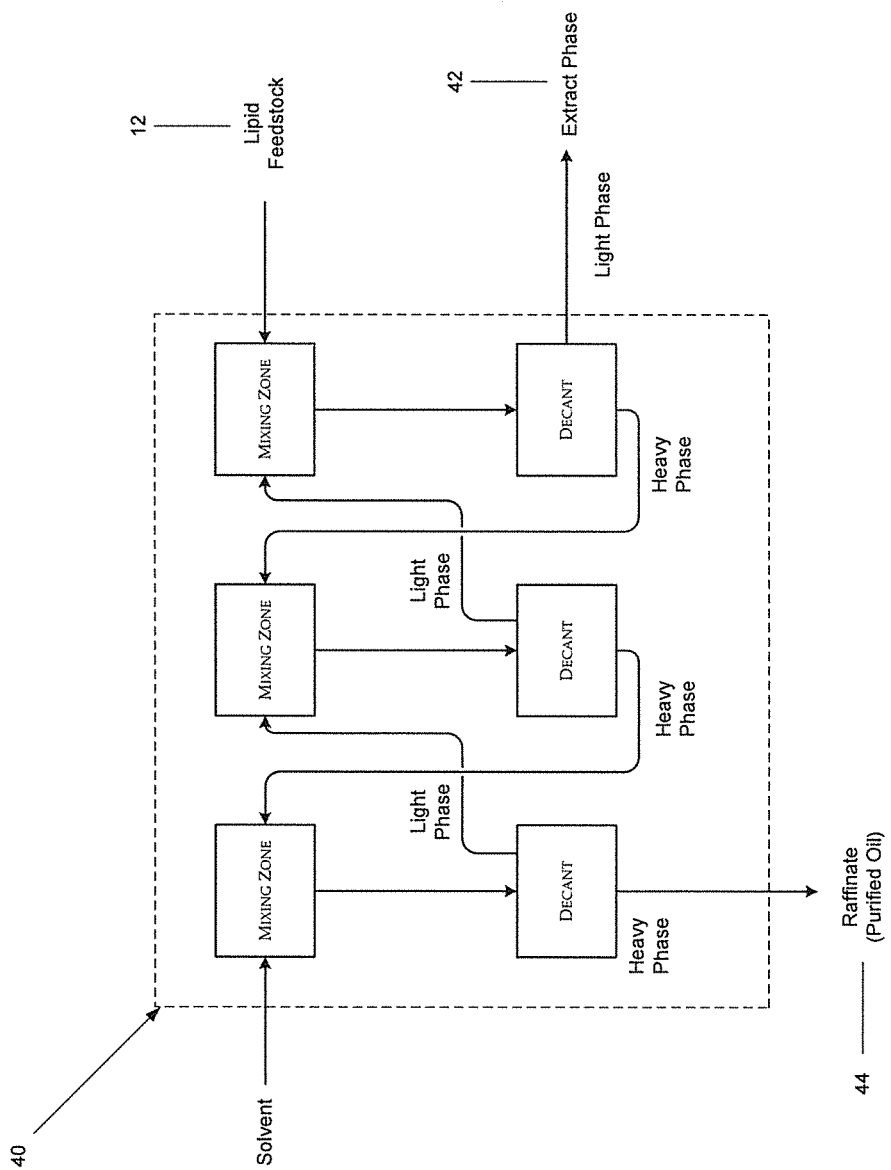
FIG. 3 is a flowchart of a third embodiment of the invention, in which a countercurrent extraction process is utilized to improve solvent efficiency.

Thus, in another embodiment of the invention, shown in FIG. 3, the lipid feedstock (12) is mixed with the solvent in a series of countercurrent wash steps (40) until the raffinate phase or the extract phase meets the desired specifications. The extract phase (42) is collected as the light phase. The raffinate phase (44) is collected as the heavy phase. In another embodiment, the solvent can be evaporated and recovered for reuse and the concentrate phase can be recovered.

The countercurrent wash steps can be further optimized through the use of various liquid to liquid extraction columns which are well known to those skilled in the art and incorporate numerous mix zones and decantation zones. Examples of continuous extraction columns are those offered by Sulzer Chemtech Ltd. including "Kuhni" agitated columns, packed columns, and mixer-settler columns.

The concentrate phase can be further processed to isolate the various extracted compounds. The concentrate phase can be subjected to saponification by adding alkali at various molar ratios. At high levels of alkali to concentrate ratios, some or all of the glycerides convert to free fatty acids and then some or all of the free fatty acids convert to soaps. The soaps are water soluble and can be removed by water washing the concentrate and separating by various methods, including, but not limited to quiescent decantation and centrifugation. The saponification process is reversible. The soaps can be converted back to free fatty acids by adding an acid to the soap solution. The free fatty acids are not soluble in water and can be recovered by various methods, including, but not limited to, quiescent decantation or centrifugation. At low levels of alkali to concentrate ratios, little or no glycerides are converted to free fatty acids; however, the free fatty acids present in the concentrate convert to soaps. The free fatty acids can be recovered using the process detailed above.

The presence of phospholipids interferes with the saponification process by acting as an emulsifier. In conventional vegetable crude oil refining, phospholipids, also known as phosphatides, are first removed by degumming (A. J. Dykstra, Degumming—Introduction, *AOCS Lipid Library*). In the degumming process, water or acidic water is mixed with the oil to solubilize hydratable phosphatides. The free fatty acids of degummed oil can then be processed by caustic refining, a saponification process. Thus, in an embodiment of the present invention, the concentrate phase can be degummed prior to saponification.

Figure 4:
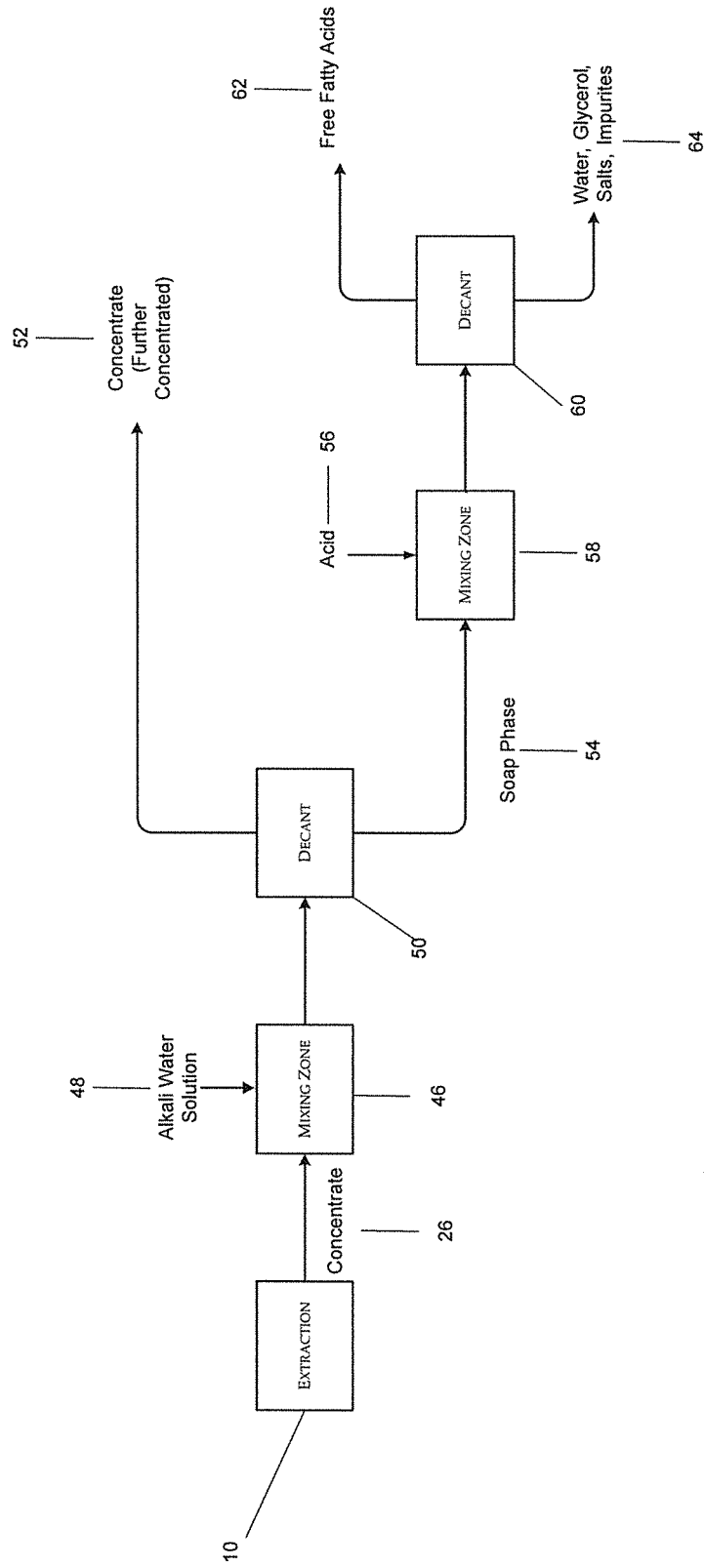
FIG. 4 is a flowchart of a fourth embodiment of the invention in which the non-glyceride concentrate of previous figures is further concentrated by removal of free fatty acids via saponification of acyl glycerides and free fatty acids with alkali water to produce a soapstock and subsequent acidification of the soapstock allows recovery of a concentrated free fatty acid stream and a mixture of water, glycerol, salts and other impurities.

In another embodiment of the invention, shown in FIG. 4, a lipid feedstock is processed as in FIG. 1 (10); the concentrate phase (26) is mixed (46) with an alkali water solution (48) and then separated by decantation (50). The light phase is collected as a further concentrated Concentrate. The soap phase (54) is collected as the heavy phase and contains soaps, water and glycerol. Acid (56) is added to the soap phase, mixed (58) and then decanted (60). Free fatty acids

(62) are removed as the light phase of the acid mixture. The heavy phase contains water, glycerol, salts and other impurities (64).

In another embodiment, the water, glycerol, salts and other impurities can be further separated. In another embodiment, the glycerol can be further processed to increase purity.

Glycerol is used by the cosmetic and personal care industry as a humectant, i.e. a substance that promotes the retention of water. Therefore, the glycerol recovered by the present invention can be used as or an additive to a cosmetic or personal care product.

The raffinate phase can be processed into alcohol esters with various methods including transesterification. The raffinate phase can also be reacted with hydrogen and products of this reaction can be recovered and separated from the reacted oil.

Therefore, another embodiment of the present invention further includes mixing the raffinate phase with an alcohol and a transesterification catalyst to produce alcohol esters and glycerol. The present invention provides for the alcohol esters and glycerol produced by these methods. Another embodiment of the present invention includes reacting the raffinate phase with hydrogen to produce one or more of the following: alkynes, naphtha, and other hydrocarbons. The present invention provides for the alkynes, naphtha, and other hydrocarbons produced by these methods.

As a result of the process described above, some of the triglycerides dissolve in the solvent and can be recovered with the extracted compounds. The triglycerides can act as a carrier as an effective method to deliver the cosmetic, personal care or skin care product. Therefore, the value of the triglycerides can be realized in the marketing of the extracts.

However, other cosmetic, personal care or skin care products would consider high levels of triglycerides or certain fatty acids, free fatty acids and/or some of the extracted compounds or other components as deleterious or undesirable. Various methods can be used to further concentrate the extracted compounds and/or remove unwanted components.

Prior to mixing with solvents, the lipid feedstock can be vacuum distilled to remove water and/or free fatty acids. Oil is heated and held under vacuum such that water and/or free fatty acids are volatilized. The water and/or free fatty acids can be removed, condensed, and collected. Separation of free fatty acids from deodorizer distillates by molecular (short path) distillation has been described by Martins et al. (*Separation and Purification Technology*, 2006, 48, 78-84).

Distillation can also be used to recover specific fatty acids based on relative volatility and boiling points. Oil is heated to the boiling point of the desired fatty acid. Fractional distillation can be used to recovery multiple fatty acid streams. Distillation can be performed at a pressure less than atmospheric to reduce the required temperature. The feedstock for the process can be any of the products of the current invention. Various methods may be employed to increase the free fatty acid content prior to distillation.

Prior to mixing with solvents, the lipid feedstock can undergo winterization. In the winterization process, the feedstock is chilled to precipitate compounds with high melting points such as saturated fatty acids. Various solvents can be added to the feedstock prior to winterization. The precipitated compounds can be removed by various methods, including, but not limited to quiescent decantation, centrifugation, or filtering. The feedstock for winterization can be the lipid feedstock, the raffinate phase, the extracted phase or the concentrate phase.

A lipid feedstock containing high melting point components can be undesirable. For example, high levels of palmitic acid will cause a lipid feedstock to solidify at room temperature. If a cosmetic or personal care product is to remain liquefied at room temperature, the palmitic acid must be removed from the lipid feedstock. If a cosmetic or personal care product is to be solidified at room temperature, palmitic acid can be added to lipid feedstock.

Prior to mixing with the solvent, the lipid feedstock can undergo degumming, deodorization, winterization, bleaching, or combinations thereof.

One embodiment of the present invention includes subjecting a feedstock to one or more of the following processes: winterization, vacuum distillation, degumming, bleaching, or deodorizing. Another embodiment of the present invention further includes wherein the feedstock is one of lipid feedstock, raffinate phase, extractable phase, or concentrate phase.

Any residual color can also be removed, such as from the low FFA raffinate oil, by bleaching. Bleaching with, for example, bleaching clay removes color bodies such as carotenoids. For example, the raffinate oil can contain less than about 1 ppm total carotenoids.

Residual color can be undesirable when using triglycerides as a carrier for certain lipid soluble components. Therefore, in one embodiment, raffinate oil with less than about 1 ppm carotenoids is used as or an additive to a cosmetic or personal care product.

Winterization of the lipid feedstock containing glycerides is only marginally effective because the glycerides can be composed of different fatty acids, thereby having different melting points than the individual fatty acids that make up the glyceride. The melting points of free fatty acids are dependent on their chain length and degree of saturation. To improve on this process, the glycerides can be converted to free fatty acids prior to winterization. Various methods can be used including, but not limited to, acid hydrolysis, enzymatic hydrolysis, caustic hydrolysis, or any other suitable method. After winterization, the free fatty acids can be converted back to glycerides.

Therefore, one embodiment of the present invention includes converting some or all of glycerides in a feedstock to free fatty acids. Another embodiment of the present invention further includes cooling the feedstock to a temperature sufficient to precipitate one or more of the free fatty acids. Another embodiment of the present invention further includes cooling the feedstock to selective temperatures to preferentially precipitate various free fatty acids. Another embodiment of the present invention includes recovering the various free fatty acids and glycerol. The present invention provides for the free fatty acids and glycerol recovered by these methods. Another embodiment of the present invention comprises converting some or all of the free fatty acids to glycerides. More specifically, prior to mixing, all or a portion of triacylglycerides in the lipid feedstock can be converted to free fatty acids by at least one process such as thermal hydrolysis, hydrothermal hydrolysis, acid hydrolysis, base hydrolysis enzymatic hydrolysis, and combinations thereof. Also prior to mixing, a portion of the free fatty acids arising from triacylglyceride hydrolysis can be removed by at least one process such as shortpath or molecular distillation, saponification and phase separation, winterization, and combinations thereof.

Winterization can also be effective on fatty acids esterified with an alcohol. Any suitable process can be used to esterify the fatty acids including, but not limited to, acid esterification and transesterification. Enzymes can be used as a catalyst for the esterification processes.

The free fatty acids can be removed from any of the phases by mixing the phase with a caustic solution in a process known as saponification. The free fatty acids form a soap that is water soluble and can be removed by washing with water. The free fatty acids can be recovered by neutralizing the water/soap mixture with an acid, reversing the saponification reaction, converting the soaps to free fatty acids. The free fatty acids can be removed and recovered from the water.

The free fatty acids can be separated through various forms of chromatography including, but not limited to, ion exchange, size-exclusion, reverse phase, and two-dimensional. In certain circumstances, individual fatty acids are desirable and can be isolated using different forms of chromatography. In other circumstances a combination of fatty acids are desirable.

Therefore, one embodiment of the present invention provides for free fatty acids and methods to recover them. Free fatty acids have utility in cosmetic and personal care products. Free fatty acids are absorbed by the skin more readily than triglycerides. Individual free fatty acids are used for a variety of purposes. As described above oleic acid, linoleic acid, and palmitoleic acid are examples of individual free fatty acids that have specific functionalities. Therefore, in one embodiment, free fatty acids are used as or additive to a cosmetic or personal care product.

Any of the phases can be saponified, transesterified, and then optionally winterized. For example, the concentrate phase can be mixed with a caustic solution to convert the free fatty acids to soaps. Water can be added to the solution to dissolve the soaps. The water and soaps can be removed by quiescent decantation. The remaining concentrate phase can be recovered, dehydrated, heated, and mixed with any suitable alcohol such as methanol and any suitable catalyst such as sodium methylate causing the glycerides to be converted to alcohol esters and glycerin. The glycerin can be removed by quiescent decantation. Any suitable acid such as hydrochloric acid may be added to aid in the removal of glycerin and the recovery of the alcohol esters. The alcohol esters can be washed with water and dehydrated. The extracted compounds will remain with the alcohol esters throughout the process. The alcohol esters can then be winterized using the process described above.

The esterification process is reversible. The alcohol esters can be heated and mixed with glycerin to convert the alcohol esters to glycerides.

All or a portion of the raffinate phase, the extract phase or the concentrate phase can undergo any one or combination of winterization, esterification, saponification, or vacuum distillation to provide a unique composition. Therefore, one embodiment of the present invention includes subjecting a feedstock to one or more of the following processes: winterization, esterification, saponification, and vacuum distillation. The feedstock can be one or more of the following: lipid feedstock, raffinate phase, extract phase, and concentrate phase.

The fatty acids present in the raffinate, extract, or concentrate phase can be saturated or unsaturated. Saturated fatty acids can be more desirable than unsaturated fatty acids in certain applications. Unsaturated fatty acids can be converted to saturated fatty acids by various methods. In one method, a feedstock containing unsaturated fatty acids is mixed with an appropriate enzyme to convert the unsaturated fatty acids into saturated fatty acids. In another method, a feedstock containing unsaturated fatty acids is reacted with an appropriate catalyst to reduce the carbon-carbon double bond. The feedstock can be the lipid feedstock, the raffinate phase, the extract phase, or the concentrate phase.

One embodiment of the present invention includes converting glycerides to free fatty acids using any suitable method. Another embodiment of the present invention further includes winterizing to selectively recover various saturated fatty acids. Another embodiment of the present invention further includes processing to convert the unsaturated fatty acids to saturated fatty acids. Another embodiment of the present invention further includes converting the unsaturated fatty acids to saturated fatty acids and winterizing to selectively recover various converted saturated fatty acids. In one embodiment of the present invention, the glycerides are contained in one or more of the following: lipid feedstock, raffinate phase, extract phase, or concentrate phase. Another embodiment of the present invention includes one or more of the following: free fatty acids, saturated fatty acids, or unsaturated fatty acids.

One embodiment of the invention includes separating one of more of the following: lipid feedstock, raffinate phase, extract phase, or concentrate phase by various forms of chromatography including, but not limited to, ion exchange, size-exclusion, reverse phase, and two dimensional. In certain circumstances individual components are desirable and can be isolated using different forms of chromatography. In other circumstances, a combination of components is desirable. Therefore, one embodiment of the present invention includes isolating one or more individual components from one of more of the following: lipid feedstock, raffinate phase, extract phase, concentrate phase.

The products, co-products and by-products produced can also be used in or as a feedstock for nutraceuticals, bio fuels, bio-lubricants, oleo chemicals, nutritional products, and other bio-products.

The present invention also provides for a method of purifying biofuel feedstock by removing color compounds, free fatty acids, and waxes from a biofuel feedstock, and recovering a purified biofuel. Each of the extract compounds can be removed as well as recovered if desired as described above. By removing these extracts, the biofuel that is produced is more pure than previous biofuels.

Biodiesel producers prefer lipid feedstocks having low levels of free fatty acids (typically less than 2% w/w and more preferably less than 1% w/w) as free fatty acids neutralize and therefore deactivate basic catalysts such as sodium methoxylate used in the transesterification step. In order to accommodate higher levels of free fatty acids biodiesel producers can deploy a two-stage esterification process in which free fatty acids are first converted to alkyl esters with an acid catalyst in a first stage followed by a conventional base catalyzed second stage transesterification. The two-catalyst process is not desirable as it adds capital cost, operating cost, and process complexity. The present invention provides for a biodiesel feedstock low in free fatty acids, thus allowing the biodiesel producer to avoid the cost and complexity of a two catalyst process.

Figure 5:
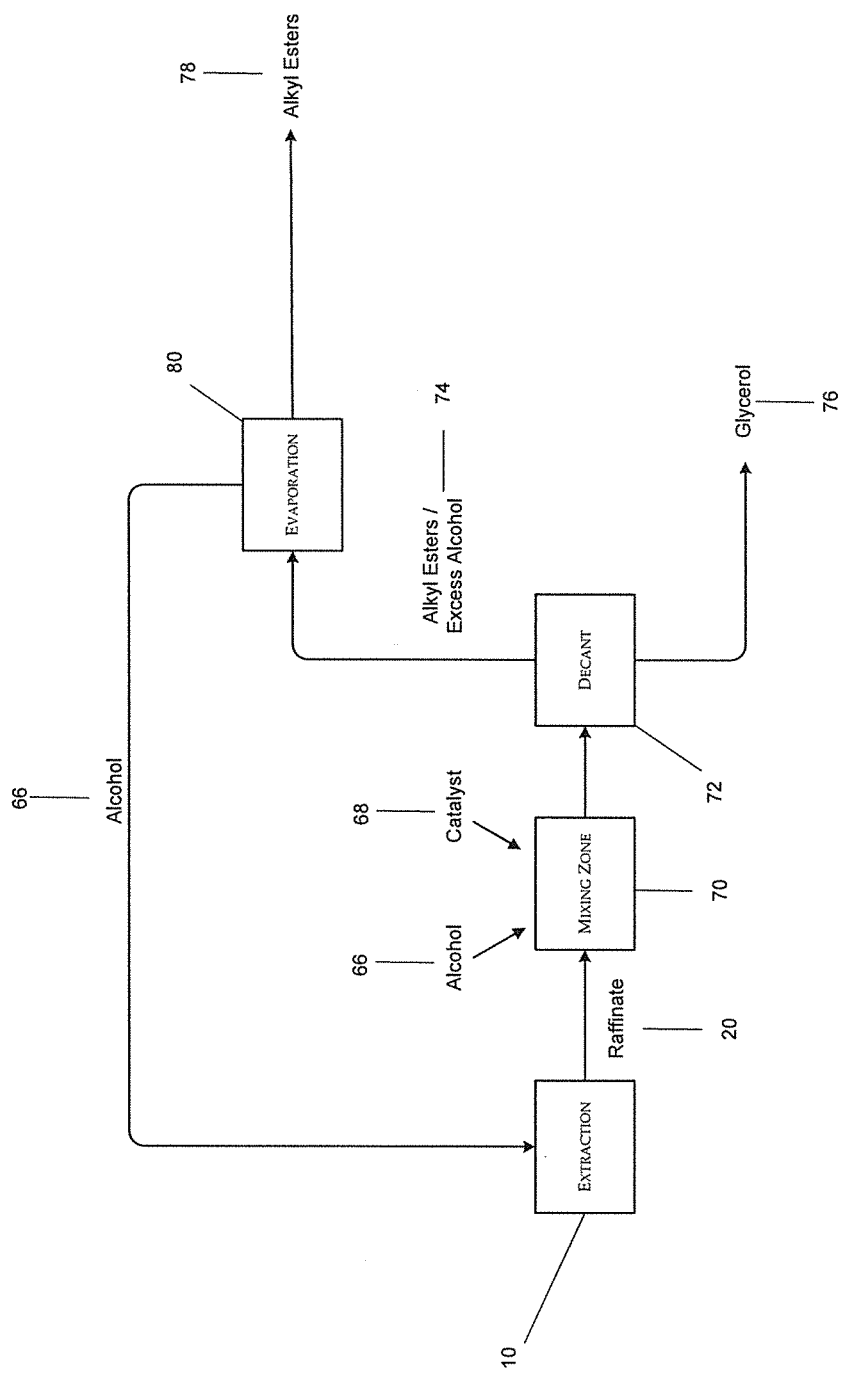
FIG. 5 is a flowchart of the method of the present invention incorporated into a fatty acid alkyl ester production process.

FIG. 5 shows a method of producing alkyl esters with a process of the present invention. A lipid feedstock is processed as in FIG. 1 (10) to produce a raffinate (20). An alcohol (66) such as methanol or ethanol and a catalyst (68) is mixed (70) with the raffinate. The transesterification process is reversible so an amount of alcohol above the stoichiometric requirements must be added to drive the reaction toward the creation of alkyl esters. The mixture is decanted (72) and the alkyl esters and excess alcohol (74) are collected as the light phase. Glycerol (76) is collected as the heavy phase. The alcohol (66) is separated from the alkyl esters (78) by, for example, evaporation (80). The alcohol can be recycled and used as the solvent in the extraction process (10).

Thus, in one embodiment of the present invention free fatty acids and beneficial non-glyceride compounds are removed from lipid feedstock by extraction with a solvent. The raffinate phase is purified oil preferably containing less than about 4% w/w FFA and greater than 96% w/w triacylglycerides. More preferably the raffinate phase contains less than 2% w/w FFA and greater than 98% w/w triacylglycerides. Most preferably the raffinate phase contains less than 1% w/w FFA and greater than 98.5% w/w triacylglycerides. The purified raffinate phase is transesterified with an alcohol to produce an alkyl ester. In one embodiment, the alcohol can be the same alcohol used in the extraction process or in another embodiment, a different alcohol can be chosen for transesterification. Any suitable basic catalyst such as liquid soluble sodium methylate or a solid phase catalyst can be used to convert the glycerides to alkyl esters and glycerin. The glycerin can be removed by quiescent decantation. Any suitable acid such as hydrochloric acid may be added to aid in the removal of glycerin and the recovery of the alkyl esters. The alkyl esters can be washed with water and dehydrated. In another embodiment the alkyl ester is used as a biofuel.

More specifically, the present invention provides for a method of producing a fatty acid alkyl ester by extracting a lipid feedstock with an alcohol to produce an extract phase and a low free fatty acid (FFA) raffinate phase, reacting the low FFA raffinate with alcohol to produce a fatty acid alkyl ester, recovering excess alcohol from the reacting step, and recycling recovered alcohol to the extraction step. The recovered alcohol can be dehydrated prior to recycling to the extracting step.

The process of the present invention can also be physically integrated or proximally located with a fatty acid alkyl ester or biodiesel production facility. The lipid feedstock can be raw materials, products, co-products, by-products, or intermediates of the fatty acid alkyl ester or biodiesel facility. The solvent can be an alcohol or an alcohol/water composition and can be a raw material, co-product, by-product, and intermediate of the fatty acid alkyl ester or biodiesel facility. The alcohol or alcohol/water composition can be recycled to the integrated or proximately located fatty acid alkyl ester or biodiesel facility after it is used in the production of the oil compositions.

The raffinate can be bleached or winterized prior to transesterification. Any residual solvent in the raffinate phase can be used for the transesterification process. The recovered solvent from the extraction process can be mixed with the recovered solvent from biodiesel process for further dehydration.

Recently, bio-lubricants have commanded a larger percentage of the lubricant market at the expense of petroleum based lubricants. They are found in areas where contamination from petroleum products is of concern such as in food production and preparation equipment. Other uses include areas where total loss of the product to the environment is expected to occur such as use in marine equipment, agricultural equipment, chainsaws, transformers, and transmission lines.

Bio-products are replacing traditional products in many areas, especially where there is heightened environmental awareness. The list of bio-based products is long and continually expanding but a few examples include degradable plastics, paints, solvents construction materials, carpet, and textiles.

The raffinate, extracted phase, and concentrate phase can be processed to produce desired compositions of components by various methods of the present invention. The compositions can be used in cosmetic, personal care, and skin care products. The compositions can be used in or as a feed stock for nutraceuticals, bio fuels, bio-lubricants, oleo chemicals, nutritional products and other bio-products.

Therefore, one embodiment of the present invention provides for a composition including at least one of the following: free fatty acids of about 15% w/w or greater, triglycerides of about 75% w/w or less, and at least one further beneficial non-glyceride compound including α-tocopherols of about 50 ppm w/w or greater, total tocopherols of about 2000 ppm w/w or greater, total carotenoids of about 300 ppm w/w or greater, lutein of about 100 ppm w/w or greater, zeaxanthin of about 100 ppm w/w or greater, and levels of total sterols of about 2000 ppm w/w or greater.

In one embodiment, the present invention provides for a lipid composition including at least one of the following: free fatty acids of 4% w/w or less, total carotenoids of about 100 ppm w/w or less, and triglycerides of greater than 96% w/w. More preferably, the lipid composition includes a triglycerides content not less than 96% w/w, free fatty acids content not greater than 4% w/w, total moisture and insolubles content not greater than 1.5% w/w, total carotenoid content not greater than 50 ppm w/w, and at least one component selected from total lutein content not greater than 50 ppm w/w, cis-lutein/zeaxanthin content not greater than 10 ppm w/w, α-cryptoxanthin content not greater than 5 ppm w/w, β-cryptoxanthin content not greater than 5 ppm w/w, α-carotene content not greater than 0.5 ppm w/w, and cis-β-carotene not greater than 0.1 ppm w/w. In a more preferred embodiment of the lipid composition, the free fatty acid content is 2% w/w or less and triglycerides are greater than 98% w/w. In a most preferred embodiment of the lipid composition, the free fatty acid content is 1% w/w or less and triglycerides are greater than 98.5% w/w. Also, more preferably, the total carotenoid content is not greater than 1 ppm w/w.

In one embodiment, the present invention provides for a lipid composition including: free fatty acids of about 5% w/w or less and total carotenoids of about 500 ppm w/w or greater.

In one embodiment, the present invention provides for a composition including a concentration of a lipid component selected from the following wherein the concentration w/w of the lipid component is at least twice the concentration of the lipid component in the lipid feedstock: free fatty acids, α-tocopherols, total tocopherols, total carotenoids, lutein, zeaxanthin, and total sterols.

In one embodiment, the present invention provides for a composition including a concentration of a lipid component selected from the following wherein the concentration w/w of the lipid component is one half or less of the concentration of the lipid component in the lipid feedstock: free fatty acids, α-tocopherols, total tocopherols, total carotenoids, lutein, zeaxanthin, and total sterols.

In one embodiment of the present invention, the compositions are derived from a lipid. The lipid can be naturally occurring. In one embodiment of the present invention, the naturally occurring lipid can be sourced as a co-product or by-product of agriculture, feed, food, or fuel processes, including, but not limited to, a grain ethanol plant. The grain ethanol plant can process one or more of the following: corn, milo, wheat, or barley. In another embodiment, the present invention provides for a composition wherein such composition is isolated from one or more of the following: corn oil and oil recovered from a fermentation process. In another embodiment of the present invention, the oil can be recovered from a fermentation process after at least one product of fermentation has been removed from said process.

The process can be further economized by co-locating with other processes, such as alcohol or biodiesel production. Such co-location reduces capital and operating expense.

The co-location of the process with alcohol production, such as ethanol, allows for several synergistic operations. In an ethanol production process grain is milled, slurried and treated with enzymes to release sugars. The sugars are fermented in a fermenter. The resultant product is referred to as "beer". The ethanol form the beer is removed by a beer column producing rectifier feed. The rectifier removes more water from the ethanol. The product is sent to a dehydration unit, such as a molecular sieve to produce high proof ethanol. The residual product from the beer column is referred to as "whole stillage." Whole stillage can be centrifuged into wet cake and thin stillage. The wet cake can be dried to produce dried distiller's grain. Some of the thin stillage can be concentrated and added to either the wet cake or dried distiller's grain. Distillers oil can be recovered at various points in the process, such as from the grain slurry, whole stillage, or thin stillage. Ethanol can be used as the solvent in the extraction process and can be obtained from various points. Ethanol can be obtained after the beer column, where the ethanol concentration is typically around 50% w/w; from the rectifying column, where the ethanol concentration is typically 95% w/w; or from the molecular sieve or other dehydration unit, where the concentration is typically over 98% w/w.

During the extraction process the ethanol can pick up moisture. This wet ethanol can be returned to the ethanol process for dehydration. The wet ethanol can be returned to one or more of the following points in the process: the fermenter, the beer well, the rectifier feed, dehydration unit feed, or any other suitable place.

Any of the compositions and products of the present invention can be added to co-products of the ethanol process, such as the wet cake, distillers solubles (syrup), dried distillers grain (DDG), high protein meal, or dried distillers grain with solubles (DDGS). For example, the raffinate or phospholipid phase can be added to the dried distiller's grain to increase its fat level. Any of the lipid compositions can be removed from a lipid feedstock and added to a distillers grain co-product. The lipid feedstock can be distillers oil such as distillers corn oil.

Various methods can be used to extract other co-products from the ethanol process that are suitable for adding products of the present invention. For example, Bleyer, et al. in US application 2014/0343259 A1, describe a method for extracting a high protein meal. The high protein meal form this process or other suitable process can be added to the extracted phase or extracted phase concentrate to produce a high protein, high carotenoid animal feed product.

Figure 6:
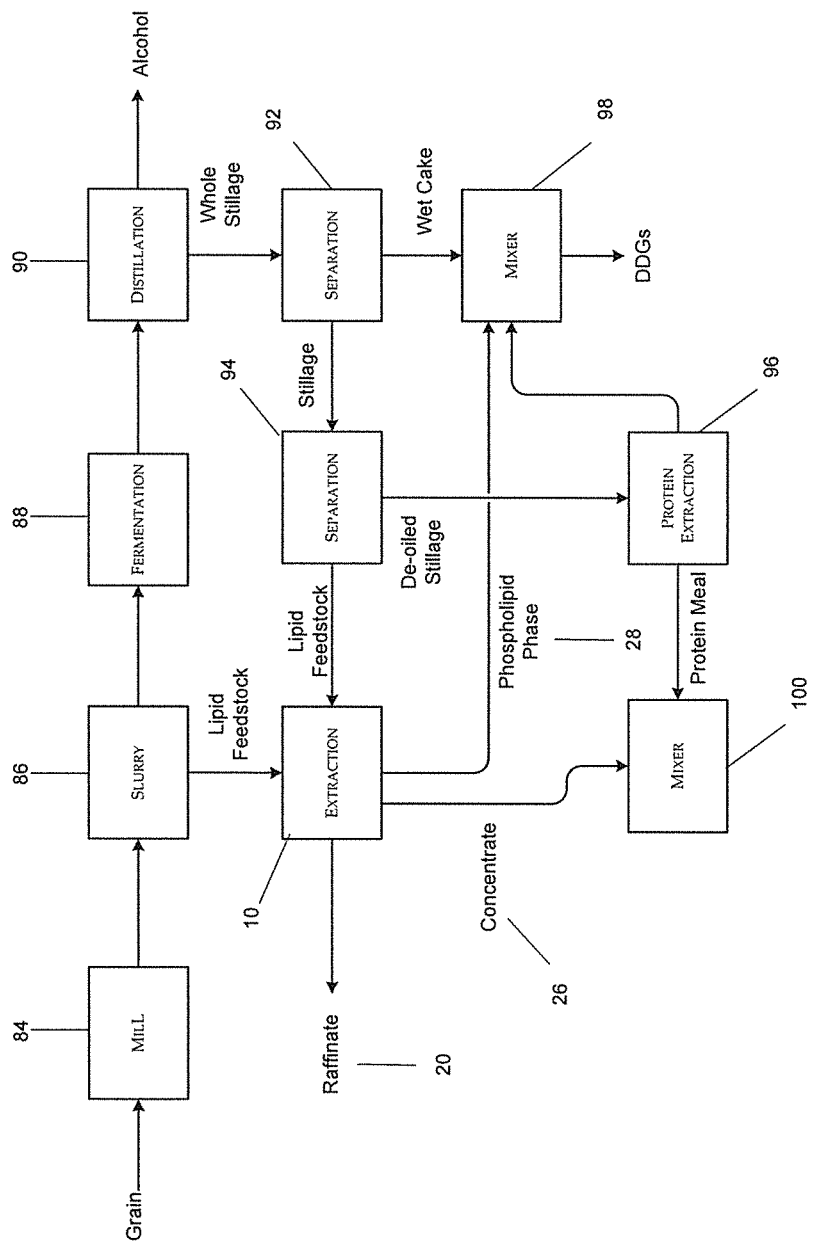
FIG. 6 is a flowchart of the method of the present invention incorporated into an ethanol production process.

FIG. 6 depicts the integration of a lipid extraction process with a alcohol production facility. Grain is milled (84), slurried (86) and fermented into an alcohol to produce a beer. The beer is distilled (90) and alcohol and whole stillage are recovered. The whole stillage is separated (92) into stillage and wet cake. The stillage is separated (94) into a lipid feedstock and a de-oiled stillage. Alternatively, a lipid feedstock can be recovered prior to fermentation, e.g. from the grain slurry (86). A high protein meal can be extracted (96) from the de-oiled stillage. The balance of the de-oiled stillage can be mixed (98) with the wet cake to produce DDGS. The concentrate (26) resulting from the extraction (10) can be mixed (100) with the protein meal to produce a high protein meal enriched with carotenoids. The phospholipid phase (28) can be mixed (98) with the wet cake to increase the fat of the DDGS.

United States ethanol producers are sensitive to the total protein plus fat content ("ProFat") of DDGS as their customers, the livestock growers, seek a threshold ProFat level for DDGS incorporation into animal rations. The primary source of fat in DDGS is residual oil from the fermented grain. Over the past decade, growers have accepted DDGS with reduced fat content as ethanol producers remove and sell more distillers oil. High protein meals derived from distillers grains command significantly higher prices than DDGS, and thus, although advantageous to the ethanol producer, further decreases the ProFat value of DDGS.

In one embodiment of the present invention, distillers oil can be fractionated to produce valuable lipid compositions, e.g. a concentrate containing beneficial non-glyceride compounds. Any of the recovered phases can be returned to the DDGS to help maintain ProFat specifications. The concentrate can be further concentrated in BNGs by removal of FFAs and glycerides, which can also be added to DDGS to maintain ProFat content.

Thus, in one embodiment, distillers oil from a fermentation facility is fractionated into the compositions of the present invention, a valuable lipid composition is isolated, and some or all of the remaining compositions can be incorporated into dry distillers grains (DDG) or DDGS. The fractionation and isolation of the lipid composition can be performed as described in the steps above.

Therefore, in one embodiment, the process of the present invention can be integrated or proximately located with a fermentation facility such as an alcohol facility. Compositions of the present invention can be removed from a lipid feedstock of the fermentation facility/alcohol facility and added to other co-products of the facility. The solvent and lipid feedstocks can be products, co-products, by-products, or intermediates of the fermentation facility. The solvent can be an alcohol or an alcohol/water composition of product, co-product, and intermediate stream of an alcohol fermentation facility. The solvent can be an alcohol or an alcohol/water composition chosen from the group consisting of product, co-product, and intermediate stream of an alcohol fermentation facility. The alcohol or alcohol/water composition can be recycled to the integrated or proximately located fermentation facility after it is used in the production of the lipid compositions. The lipid feedstock can be distillers oil, such as distillers corn oil, obtained from a pre-fermentation or post-fermentation process stream.

The present invention also provides for a method of producing a distiller's product by separating a lipid from a fermentation process, mixing the lipid with a solvent and obtaining a lipid/solvent mixture, separating the lipid/solvent mixture into two or more fractions, and adding at least some of the one or more fractions to at least a portion of fermentation stillage. Each of these steps are described above.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Ethanol and Methanol Extractions of DCO

A sample of distillers corn oil (DCO) produced by separation from the stillage syrup using a disc stack centrifuge was obtained from a corn ethanol plant. The DCO was extracted in the laboratory with anhydrous ethanol and methanol as follows.

Method: Two 50 ml samples of DCO were accurately weighed into separate 250 ml Erlenmeyer flasks, each flask containing a magnetic stir bar and a weighed volume of approximately 50 ml ethanol or methanol respectively. The flasks were stirred for 120 minutes at room temperature and then allowed to quiescently phase separate for 60 minutes. The light phase containing the extract from each flask was decanted and weighed. The heavy raffinate from each flask was weighed. Solvent was removed from the light phase by rotovap at 60 C under vacuum to produce a first concentrate. The heavy raffinate was extracted twice more with 50 ml with fresh ethanol or methanol respectively following the same extraction procedure. A second and third concentrate was collected after solvent removal by rotovap. The final raffinate (purified oil) and a sample of the original DCO were also retained for analysis.

The concentration of carotenoids was determined by absorbance at 445 nm of the sample dissolved in ethanol. The glyceride and free fatty acid concentrations were determined by correlating, to a standard calibration curve, the FT-IR absorbance of the 1744 cm$^{-1}$ peak for ester bond and the 1710 cm$^{-1}$ for carboxylic acid peak, respectively.

Results: The results are shown in TABLE 1.

TABLE 1

Concentration of Carotenoids, Glycerides, and FFAs

| | | Carotenoids % w/w | Glycerides (TAGs + DAGs) % w/w | Free Fatty Acids (FFAs) % w/w |
|---|---|---|---|---|
| | DCO | 0.03 | 88 | 12 |
| Ethanol | Purified Oil (final raffinate) | 0.02 | 98 | 2 |
| | First Concentrate (solvent free extract) | 0.13 | 62 | 38 |
| Methanol | Purified Oil (final raffinate) | 0.03 | 98 | 2 |
| | First Concentrate (solvent free extract) | 0.20 | 42 | 58 |

The percentage of glycerides in the oil increased from 88% in the feedstock (DCO) to 98% in the raffinate (purified oil) for both methanol and ethanol extractions. The concentrate from methanol and ethanol extractions both showed significantly higher free fatty acid and carotenoid levels as compared with the DCO feed. Both ethanol and methanol are polar solvents; however, ethanol is more hydrophobic than methanol. The greater hydrophobicity of ethanol resulted in increased levels of glyceride oils (TAGs and DAGs) partitioning into the extract phase at the expense of FFAs and carotenoids. Conversely, the lesser hydrophobicity of methanol results in greater partitioning of FFAs and carotenoids into a methanol extract phase versus ethanol. EXAMPLE 1 demonstrates the effectiveness of polar solvents and that the composition of the recovered oil fractions can be tailored through proper solvent selection.

EXAMPLE 2

Ethanol Extraction of DCO

A sample of distillers corn oil (DCO) produced as described in EXAMPLE 1. The DCO was extracted twice with anhydrous ethanol at a 3:1 solvent/feed mass ratio.

Method: Two 50 ml samples of DCO were accurately weighed into separate 250 ml Erlenmeyer flasks, each flask containing a magnetic stir bar and 150 ml ethanol. The flasks were stirred for 120 minutes at room temperature and then allowed to quiescently phase separate for 30 minutes. The extract from each flask was decanted, weighed and combined. The raffinate from each flask was weighed and combined. Solvent was removed from the combined light phase by rotovap at 60° C. with vacuum to produce a first concentrate. The combined raffinate phase was extracted again with 150 ml ethanol following the same extraction procedure and a second concentrate was collected after solvent removal by rotovap. The first and second concentrates were weighed, combined, and retained for analysis. The final raffinate oil and a sample of the original DCO were also retained for analysis. Analyses of sterols and tocopherols were based on JAOCS Vol. 60, no. 8 (August 1983). Analyses of FFAs, glycerides (MAG, DAG, TAG), tocotrienols and carotenoids were performed by POS Bio-Sciences (Saskatoon, Saskatchewan, Canada) using published and proprietary POS Bio-Science methods as follows:

Free Fatty Acids: reference AOCS Ca 5a-40. Acyl Glycerides: mono and diglycerides reference AOCS Cd 11d-96; triglycerides by POS internal method, reference AOCS Official Method Cd 11d-96. Tocotrienols: internal POS method, reference: M. Balz et al., Fat Sci. Technol., 94 Jahrgang, Nr. 6, 1992, pp 209-213 and M Balz et al., Fat Sci. Technol., 95 Jahrgang, Nr. 6, 1993, pp 215-220. Carotenoids: internal POS method: reference AOAC Official Method 970.64.; F. W. Quackenbush and R. L. Smallidge, J. Ass. Offic. Anal. Chem., 69, 767 (1986); L. C. Sander, K. E. Sharpless, N. E. Craft and S. A. Wise, Anal. Chem., 66, 1667 (1994).

Results

TABLE 2

| Compound | Unit | DCO | Final Raffinate (purified oil) | Final Concentrate (solvent free extract) |
|---|---|---|---|---|
| Astaxanthin | ppm | 12 | nd | 26 |
| Lutein | ppm | 125 | nd | 273 |
| Zeaxanthin | ppm | 97 | nd | 196 |
| Total Carotenoids | ppm | 234 | nd | 495 |
| alpha-Tocopherol | ppm | 170 | 0.07 | 280 |
| beta-Tocopherol | ppm | 10 | nd | 70 |
| gamma-Tocopherol | ppm | 990 | 0.21 | 208 |
| delta-Tocopherol | ppm | 80 | nd | 110 |
| Total Tocopherols | ppm | 1240 | 0.28 | 2600 |
| alpha-Tocotrienol | ppm | 230 | 0.04 | 510 |
| gamma-Tocotrienol | ppm | 360 | 0.05 | 690 |
| delta-Tocotrienol | ppm | 10 | nd | 50 |
| Total Tocotrienol | ppm | 600 | 0.09 | 1300 |
| beta-Sitosterol | ppm | 768 | 545 | 1160 |
| Stigmasterol | ppm | 89 | 52 | 157 |

TABLE 2-continued

| Compound | Unit | DCO | Final Raffinate (purified oil) | Final Concentrate (solvent free extract) |
|---|---|---|---|---|
| Campesterol | ppm | 314 | 199 | 521 |
| Other Sterols | ppm | 673 | 499 | 976 |
| Total Sterols | ppm | 1844 | 1295 | 2814 |
| Free Fatty Acids | wt % | 8.3 | 0.84 | 20.0 |
| MAGs | wt % | 0 | nd | 0.05 |
| DAGs | wt % | 1.28 | 0.27 | 2.91 |
| TAGs | wt % | 86.0 | 99.3 | 66.5 |

The results of the experiment are shown in TABLE 2. With two extraction stages, the percentage of triglycerides in the oil increased from 86% in the feedstock (DCO) to over 99% in the raffinate (purified oil) while reducing free fatty acids from over 8% to less than 1%. The two stage process also produced a concentrate (solvent free extract) significantly enriched in free fatty acids and the beneficial non-glyceride compounds of the families carotenoids, tocopherols, tocotrienols and sterols. Many of the BNGs were concentrated to more than twice their concentrations in the starting feedstock.

EXAMPLE 3

Bleached Raffinate

A sample of raffinate was produced as described in EXAMPLE 2. Raffinate was subjected to bleaching for color body removal.

Method: "Perform 6000" bleaching clay (Oil-Dri Corporation, USA) was added to the oil at a 5% w/w ratio. The solution was stirred and heated for 30 minutes at 93° C. The sample was centrifuged at 3000 g for 10 minutes. The supernatant was then filtered through grade 3 filter paper (Whatman Co.) to remove residual bleaching clay. The unbleached raffinate oil and resultant bleached raffinate oil were bottled under nitrogen blanket and sent to Craft Technologies for carotenoid analysis by their in-house HPLC method utilizing a C18 column.

Results:

TABLE 3

Analysis of Bleached Raffinate

| | Unbleached Raffinate | Bleached Raffinate |
|---|---|---|
| FFA (% w/w) | not determined | 1.3% |
| Iodine Value | 121 | 121 |
| MIU (% w/w) | 3.24% | 1.49% |
| Carotenoids (ug/g) | | |
| trans-Lutein | 33.3 | 0.02 |
| Zeaxanthin | 38.8 | n.d. |
| cis-Lutein/Zeaxanthin | 19.5 | n.d. |
| alpha-Cryptoxanthin | 8.8 | n.d. |
| beta-Cryptoxanthin | 13.7 | n.d. |
| alpha-Carotene | 4.6 | n.d. |
| trans-beta-Carotene | 5.5 | n.d. |
| cis-beta-Carotene | 3.3 | n.d. |
| Total Carotenoids | 127.4 | 0.02 |

*n.d.: not detected (detection limit = 0.005 μg/g)

The results of the experiment are shown in TABLE 3. A standard bleaching process applied to the raffinate reduced the majority of the carotenoids to below detectable limits and total carotenoids well below 1 ppm (1 ug/g).

EXAMPLE 4

Further Concentration of Beneficial Non-Glyceride Compounds by Shortpath Distillation (SPD)

A concentrate product from ethanol extraction of DCO was prepared as described in EXAMPLE 2. The concentrate sample was shipped to Myers Vacuum Inc. (Kittaning, Pa., USA) and distilled in a Myers Lab-3 centrifugal molecular still. The feed was preheated to 35 degrees C., loaded into a degasser and allowed to degas at 50 degrees C. until 30 mtorr was reached. The feed was then fed onto the rotor (rotor temperature was 240 degrees C.) and yielded 23.6% distillate and 76.4% residue. The distillate and bottoms fractions were collected and analyzed for carotenoids and free fatty acids by the methods of EXAMPLE 1.

Results:

TABLE 4

Analysis of Shortpath Distillation Products

| | Carotenoid mM | FFA % |
|---|---|---|
| Concentrate (SPD feed) | 0.577 | 29.8 |
| SPD Bottoms | 0.989 | 25.7 |
| SPD Distillate | 0.120 | 67.5 |

The results presented in TABLE 4 demonstrate that removal of free fatty acids by shortpath distillation increases the carotenoid concentration of the resultant distillate bottoms.

EXAMPLE 5

Continuous Extraction

A sample of DCO was obtained as described in EXAMPLE 1. DCO was heated to 70° C. and fed to the bottom and room temperature ethanol was fed to the top of a 10 ft by 4 inch rotating disc liquid-liquid extraction column at approximately 0.3 L/min each. The extract phase was allowed to quiescently decant overhead while raffinate was concurrently removed. Samples were taken at various time points during operation and analyzed for carotenoids as described in EXAMPLE 1.

Results:

TABLE 5

Analysis of Continuous DCO-Ethanol Extraction

| | Carotenoid, mM | | |
|---|---|---|---|
| Sample time, min | Feed (DCO) | Raffinate | Extract (solvent free basis) |
| 30 | 0.581 | 0.374 | 1.267 |
| 60 | 0.581 | 0.419 | 1.201 |
| 90 | 0.581 | 0.383 | 1.381 |
| 120 | 0.581 | 0.435 | 1.141 |
| 150 | 0.581 | 0.444 | 1.364 |

EXAMPLE 5 demonstrates that continuous solvent extraction of a lipid feedstock can consistently produce a concentrate (solvent free extract) having double the initial DCO concentration of carotenoids a beneficial non-glyceride compound.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A lipid composition derived from a solvent-extracted distillers oil of a dry-grind ethanol process comprising:
   free fatty acids of about 15% w/w or greater;
   triglycerides of about 75% w/w or less;
   and at least two or more beneficial non-glyceride compound chosen from the group consisting of α-tocopherol, of about 50 ppm w/w or greater, total tocopherols of about 2000 ppm w/w or greater, total carotenoids of about 300 ppm w/w or greater, lutein of about 150 ppm w/w or greater, zeaxanthin of about 100 ppm w/w or greater, and total sterols of about 2000 ppm w/w or greater.

2. The lipid composition of claim 1, wherein said lipid composition is derived from a seed, plant, vegetable, or animal-based lipid.

3. The lipid composition of claim 1, wherein said lipid composition is derived from a lipid byproduct of a fermentation process.

4. The lipid composition of claim 3, wherein said fermentation process is ethanol fermentation.

5. A cosmetic, personal care, or skin care product comprising the lipid composition of claim 1.

6. The cosmetic, personal care, or skin care product of claim 5, chosen from the group consisting of shampoos, hair lotions, skin care products, skin lotions, skin protection products, sunscreen lotion, self tanning products, nail creams, and nail polish.

* * * * *

UNITED STATES PATENT AND TRADEMARK OFFICE
CERTIFICATE OF CORRECTION

PATENT NO. : 9,889,084 B2  
APPLICATION NO. : 14/594572  
DATED : February 13, 2018  
INVENTOR(S) : Bleyer et al.

Page 1 of 1

It is certified that error appears in the above-identified patent and that said Letters Patent is hereby corrected as shown below:

On the Title Page

Item (72):  
Add Ankur Patel as an inventor

Signed and Sealed this  
Sixth Day of November, 2018

Andrei Iancu  
*Director of the United States Patent and Trademark Office*